US00PP13715P39

(12) United States Plant Patent
Murakami

(10) Patent No.: US PP13,715 P3
(45) Date of Patent: Apr. 8, 2003

(54) PETUNIA PLANT NAMED 'SUNBELKUOPI'

(75) Inventor: Yasuyuki Murakami, Shiga (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/878,239

(22) Filed: Jun. 12, 2001

(65) Prior Publication Data

US 2002/0188996 P1 Dec. 12, 2002

(51) Int. Cl.[7] ..... A01H 5/00

(52) U.S. Cl. ..... Plt./356

(58) Field of Search ..... Plt./356, 263

(56) References Cited

U.S. PATENT DOCUMENTS

PP12,086 P2 * 9/2001 Bessho et al.

OTHER PUBLICATIONS

UPOV–ROM GTITM Computer Database, 2001/06, GTI Jouve Retrieval Software, citation for 'Sunbelkuopi'.*

* cited by examiner

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

'SUNBELKUOPI' is a decumbent plant, with small and vivid purplish pink flowers, which is suitable for potting, hanging pots and flower bedding. This plant has abundant branching and secondary branching is especially strong. Leaf shape is lanceolate to elliptic with some pubescence on the surface, having a small petiole. Leaf color is dark yellowish green (RHS C.C. No.146A). The flowers are single and very small, 2.8 cm in diameter. The color of flower is vivid purplish pink (RHS C.C. No.80C). The bottom color of inside of throat is bright greenish yellow (RHS C.C.No.2B) and the outside color of corolla tube is pale yellowish green (RHS C.C. No.150D). Flowering time is late. The plant has a high resistance to heat, rain, cold and diseases.

2 Drawing Sheets

BOTANICAL/COMMERCIAL CLASSIFICATION

*Petunia hybrida*/Petunia Plant

VARIETAL DENOMINATION cv. 'Sunbelkuopi'

BACKGROUND OF THE VARIETY

The Petunia is a very popular plant that is used for flower bedding and potting in the summer season. There are only a few varieties of the Petunia plants which do not have an upright growth habit and which have a high resistance to rain, heat, cold, and diseases. The Petunias of the Revolution series include 'Revolution Purplepink' (U.S. Plant Pat. No. 6,915), 'Revolution Brilliantpink' (U.S. Plant Pat. No. 6,914), 'Revolution Brilliantpink-mini' (U.S. Plant Pat. No. 6,899), and 'Revolution Bluevein' (U.S. Plant Pat. No. 9,322). These are decumbent type plants having long stems, a low plant height, abundant branching, and a high resistance to heat, cold, and rain. However, there are only a few Petunia varieties having a great profusion of flowers, small vivid purplish-red colored flowers, and a high resistance to rain, heat, cold, and diseases. Accordingly, this invention was aimed at obtaining a new Petunia variety having small vivid purplish-red colored flowers, together with the above features.

The new variety of Petunia plant according to this invention originated from a controlled crossing involving as female parent 'CDS02' (non-patented in the United States), 'CDS02' was the product of the cross of *Petunia sellowiana Sendtu* named 'CD1' (non-patented in the United States) and a wild type of Petunia plant native to Brazil named 'A1'

(non-patented in the United States). The male parent was 'CDS01' (non-patented in the United States). 'CDS01' was the product of a cross of *Petunia sellowiana Sendtu* named 'CD2' (non-patented in the United States) and a wild type of Petunia plant native to Brazil named 'A2' (non-patented in the United States). In May, 1993, the series of controlled crosses was conducted with *Petunia sellowiana Sendtu* named 'CD1' and 'CD2', and a wild type of Petunia plant native to Brazil named 'A1' and 'A2'. From that crossing, 240 seedlings were obtained and 4 seedlings which included 'CDS01' and 'CDS02' were selected by March 1994. Subsequently, 500 seedlings were obtained from a crossing of these 4 seedlings. Ten seedlings were selected by March 1995. These 10 seedlings were propagated by the use cuttings and were grown in a trial in flower beds and in containers by October 1996. Finally, a single seedling was selected and the botanical characteristics of the plant were evaluated. As a result, it was concluded that this new variety is distinguishable from other varieties, and this variety of Petunia plant was named 'Sunbelkuopi'.

This new variety of Petunia plant named 'Sunbelkuopi' was asexually reproduced by the use of cuttings at Oomori-cho, Yokaichi-shi, Shiga-ken, Japan, and the homogeneity and stability thereof were confirmed. It commonly takes approximately two weeks to initiate the rooting of cuttings of the new variety of the present invention.

In the following description, the color identification is in accordance with The R.H.S. Colour Chart of The Royal Horticultural Society, London, England.

SUMMARY OF THE NEW VARIETY

Described herein is a decumbent type Petunia plant named 'Sunbelkuopi' having very small vivid purplish-pink flowers. The plant has abundant branching, a great profusion of blooms, and the entire plant remains in bloom for a considerable period of time. The plant is highly resistant to rain, heat, cold and disease. This new variety of Petunia plant is suitable for growing in pots, hanging baskets, and flower beds.

The plants described and depicted herein had been propagated by the use of cuttings and were approximately 28 weeks of age. Such plants were grown under controlled greenhouse conditions under full sunshine with no shielding from light. The minimum temperature at night was maintained above 13° C. The plants were fertilized on a weekly basis.

BRIEF DESCRIPTION OF THE PHOTOGRAPHS

DESCRIPTION OF THE NEW VARIETY

Figure 1:
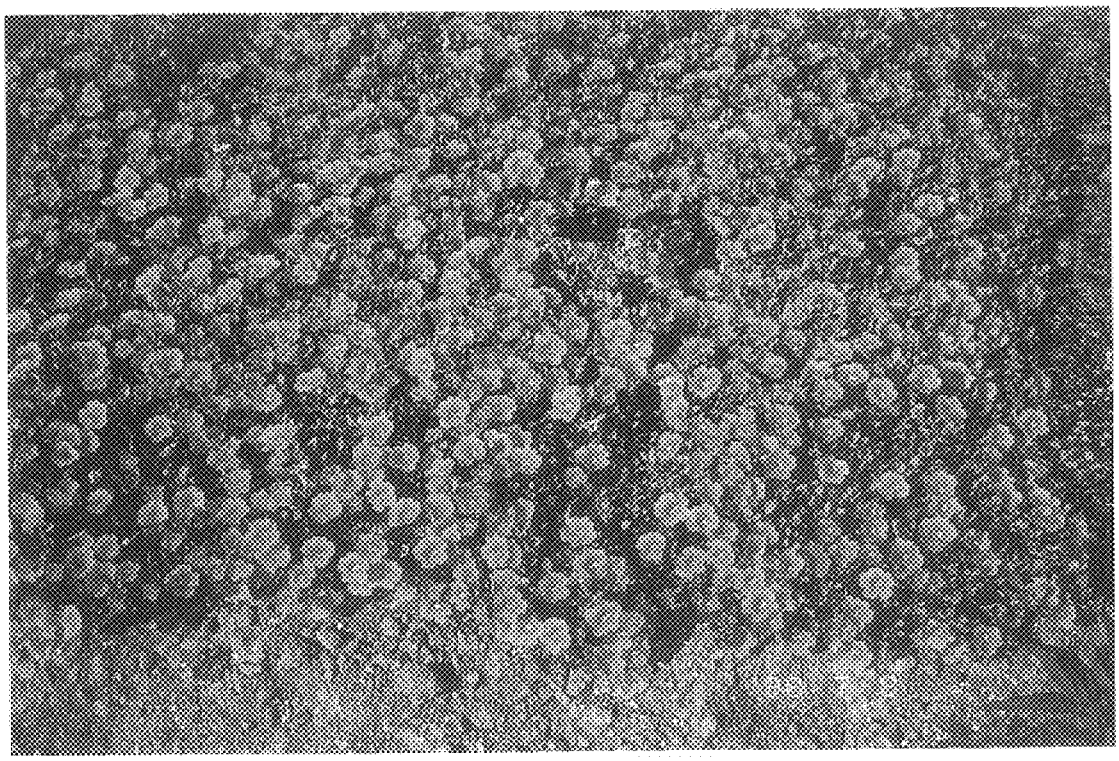
FIG. 1 shows a mass planting of the new variety of Petunia plant named 'Sunbelkuopi'.
Figure 2:
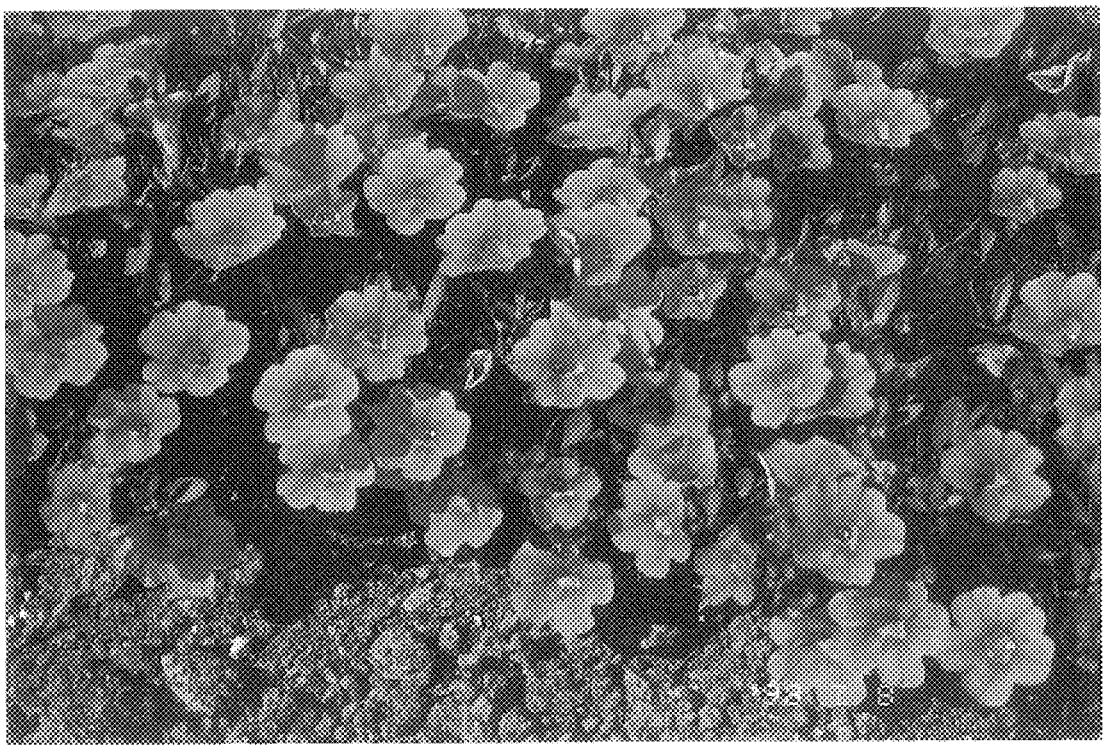
FIG. 2 shows a closer view of the flowers of the new variety of 'Petunia' plant named 'Sunbelkuopi'.

The new variety of Petunia plant named 'Sunbelkuopi' can be readily distinguished from the similar variety 'Sunbelkupi' (U.S. Plant Pat. No. 10,287) in the following areas:

1. The flower color of 'Sunbelkuopi' is vivid purplish-pink (R.H.S. No. 80C) compared to the flower color of 'Sunbelkupi' which is vivid reddish-purple (R.H.S. No. 74A);
2. The shape of leaf of 'Sunbelkuopi' is lanceolate to elliptic and is wider than the leaf of 'Sunbelkupi';
3. The surface color of the leaves of 'Sunbelkuopi' is lighter than that of 'Sunbelkupi'; and
4. The shape of the petal tip of 'Sunbelkuopi' tends to be more obverse when compared to the petal tip of 'Sunbelkupi'.

The new variety of Petunia plant named 'Sunbelkuopi' can be readily distinguished from a similar variety, 'Pearl Sky blue' (non-patented in the United States), in following areas:

1. The flower color of 'Sunbelkuopi' is vivid purplish-pink (R.H.S. No. 80C) compared to the color of 'Pearl Sky Blue' that is bluish-purple (R.H.S. No. 86C);
2. The shape of the leaves of 'Sunbelkuopi' is lanceolate to elliptic and wider than that of the leaves of 'Pearl Sky Blue';
3. The surface color of the leaves of 'Sunbelkuopi' is darker than that of 'Pearl Sky Blue'; and
4. The flower size of 'Sunbelkuopi' is smaller than that of 'Pearl Sky Blue'.

'Sunbelkuopi' is a decumbent plant, with small vivid purplish-pink flowers that is suitable for growing in pots, hanging baskets and flower beds. The spreading area of the plant is medium and the plant height is approximately 5.0 cm at the blooming time of the 5th to the 10th flower. At an age of 12 weeks, the plant width following pinching on two occasions commonly is approximately 18 cm, the main stem length is approximately 10 cm, and the plant height commonly is approximately 5 cm. The plant vigor is good as by a comparison of these dimensions to those of a plant having an age of 28 weeks. A 28 week-old plant commonly displays a plant width of approximately 50 cm, a main stem length of approximately 30 cm, and the same plant height of approximately 5 cm. The diameter of the stem is approximately 1.7 mm, and the coloration is yellow-green (R.H.S. 144C) with no anthocyanin coloration being present. This plant has abundant branching with the secondary branching being especially strong. Approximately 10 lateral branches commonly are present. The internode length is approximately 1.5 cm. The leaves are very small, approximately 3.1 cm in length, approximately 1.2 cm in width, and approximately 0.4 mm in thickness. The leaf shape is broad lanceolate to elliptic, some pubescence is present on the surface, and the leaves are substantially sessile with little or no petiole being present. The leaf color is dark yellowish-green (R.H.S. No. 146A) on the upper surface and yellowish-green (R.H.S. No. 146B) on the under surface. The leaf apex is obtuse, the leaf base is attenuate, and the leaf margin is entire. The leaf venation pattern is pinnate and the leaf vein coloration is yellowish-green (R.H.S. No. 144B).

The flower buds commonly measure approximately 20 mm in length and approximately 6 mm in diameter. The bud coloration initially is yellow green (R.H.S. 144B), and subsequently lightens (R.H.S. 150C) at the base and is pale purple (R.H.S. 77D) towards the tip.

The calyx is tubular in configuration, approximately 11.5 mm in length, and divides into five sepals. The sepal coloration is green (R.H.S. 143A), and the sepal width commonly is approximately 11 mm at the broadest point.

The flowers are single and very small, and commonly measure approximately 2.8 cm in diameter. The facing direction of the flowers is slightly upward to horizontal. The flower has a tubular corolla that divides into five petals at the apex. The typical corolla tube length is approximately 14 mm. The petal texture is smooth and the petal margins are entire. The flower petal color is vivid purplish-pink (R.H.S. No. 80C) on the upper surface, and pale purple (R.H.S. 75C) on the under surface. The base color of the inside of the throat is bright greenish-yellow (R.H.S. No. 2B), and the outside color of corolla tube is pale yellowish-green (R.H.S. No. 150D). The shape of the petal tip is obverse, the lobation is shallow, and waviness is weak. The shape of calyx is narrow. The shape of the stamens is typical of the species and 5 are present. The filaments are light yellow-green (R.H.S. 154C) in coloration, and the anthers are yellow (R.H.S. 12B) in coloration. Two of the filaments commonly are longer and bend over the pistil. The shape of the single pistil is typical for the species. During observations to date no fruits or seeds have been observed. The peduncle is approximately 1.9 cm in length, and approximately 0.8 mm in diameter.

The flowering time is late. The plant has high resistance to heat and rain. Superior tolerance to Powdery Mildew and Botrytis has been observed; however, some susceptibility is displayed. The new variety is susceptible to Root Rot and Tobacco Mosaic Virus, as well as Aphids, Whiteflies, and Thrips.

What is claimed is:

1. The new and distinct variety of Petunia plant, substantially as herein illustrated and described, characterized particularly as to novelty by (A) a decumbent growth habit, (B) abundant branching with a great profusion of blooms and the entire plant remaining in bloom for considerable period time, (C) very small single flowers having a vivid purplish-pink coloration, (D) high resistance to rain and heat, and (E) superior tolerance to Powdery Mildew, and Botrytis.

* * * * *